United States Patent [19]

Austin

[11] Patent Number: Plant 7,212

[45] Date of Patent: Apr. 3, 1990

[54] ROSE PLANT AUSLO

[75] Inventor: David C. H. Austin, Albrighton, England

[73] Assignee: David Austin Roses, Albrighton, England

[21] Appl. No.: 259,279

[22] Filed: Oct. 18, 1988

[51] Int. Cl.[4] ..... A01H 5/00

[52] U.S. Cl. ..... Plt./1

[58] Field of Search ..... Plt./1, 21

*Primary Examiner*—Howard J. Locker

*Attorney, Agent, or Firm*—Ladas & Parry

[57] ABSTRACT

A new variety of rose plant of the shrub class distinctive in its character by its fully double, dark crimson flowers with abundant, continual blooming and the unusual blend of coloring and shaping of the flower.

1 Drawing Sheet

BACKGROUND OF THE INVENTION

The present invention relates to a new and distinct variety of shrub rose, a seedling resulting from a definite effort to produce an improvement in this class of roses.

Primary features of this new variety which connote a distinctive advance over existing types are the vigorous abundant and continual blooming taken with the perfection of the fully double flowers of an old-fashioned type more particularly apparent in the accompanying illustration of a specimen thereof.

SUMMARY OF THE INVENTION

The following is a detailed description of the new variety, colour terminology being in accordance with the "Methuen Handbook of Colour" published by Eyre Methuen Ltd. (1963).

BRIEF DESCRIPTION OF DRAWINGS

The drawing depicts, from side view, stems, foliage, flower buds and flowers in various stages of developments.

DETAILED BOTANICAL DESCRIPTION

Variety Denomination (in accordance with the UPOV Convention): Auslo (Trade name Othello).

Type: Hardy; bush; outdoor; seedling; for cut flowers and garden decoration.

Class: shrub.

Propagation: holds its distinguishing characteristics through succeeding propagations by budding.

The rose plant was grown at Albrighton, Nr. Wolverhampton, England and was derived as follows:

Female parent (seed parent): Lilian Austin.

Male parent (pollen parent): The Squire.

The operation of the artificial pollination is therefore expressed by the following (Lilian Austin×The Squire).

The following observations are made of specimens grown outdoors in England.

Plant Description

Plant:

*Height.*—105 cm. on average.

*Habit.*—Robust, upright and bushy.

Branches:

*Color.*—Young stems: Deep green 28 E8 with reddish tints. Adult wood: Dark green 28 F8.

Leaves:

*Stipules.*—Medium width — margin slightly serrate or glandular hairy.

*Petiol.*—Upper side — Concave, Light green. Glandular hairy at margin. Under side — Light green — very occasional prickles and glandular hairy.

*Folioles.*—Number 5 with 3 at base of flower. Shape — ovate. Serration — dentate. Texture — Medium — fairly shiny.

*General effect.*—Dense Dark green, semi-glossy foliage.

*Color.*—Young foliage — Upper side — Brown green in color. Under side — Reddish brown in colour 9 E7. Adult foliage — Upper side — Dark green 29 F8. Under side — Greyish green 28 E6.

The inflorescence is:

Number of flowers: Solitary.

Peduncle: Straight, Rigid, and usually Red-Green. Scattered with small thorns.

Length: 6–8 cm on average.

Sepals: Upper side: Light yellow — moderately finely hairy. Under side: Glabrous, Mid-green with Red central axis. Long tip, Red at end. Edges fairly hairy with glandular hairs and some sepals are pinnately branched.

Bud:

*Shape.*—Broad with flat top.

*Length.*—2 cm. on average.

*Size.*—Medium.

*Colour.*—When opening. Upper side: Base of petal Olive Yellow 3 C8 — the rest very Dark Crimson 12 C8. Under side: Same but with bloom on the Dark Crimson 12 C8.

Flower:

Shape.—Rounded — moderately loose — regularly arranged petals.

*Diameter.*—12 cm.

*Color.*—When opening. Upper side: Yellow 3 A8 at base with majority of flower Dark Crimson 12 C8. Under side: Same, with bloom. When blooming: Upper Side— Yellow 3 A7 at base, turning to Cerise-Red 12 C7. Under Side: Deep Yellow 3 A8 at base, turning to very Dark Cerise-Crimson 11C7. Petals deepen towards centre. When finished blooming: Upper Side: Yellow 3 A7 with sharp demarcation to Purplish-Violet Red 12 C7. Under Side: Light Yellow 2 A5 turning to Greyish-Magenta 13 C6.

*Fragrance.*—Powerful Old Rose fragrance.

*Lasting quality.*—Good.

*Petals.*—Shape — Broadly ovate on the outside Texture — Silky. Number — 78 on average. Cleaning — Good.

Reproductive organs:

*Stamens.*—Number — 38. Anthers — Bright Yellow 3 A7. Filaments — Yellow 3 A4.

*Pistils.*—Number — 43. Stigmas — Straw. Styles — Light Green hairy. Receptacle — Shallow cup — Medium Green with raised Yellowish Green rim.

The development:

*Vegetation.*—Robust.

*Blooming.*—Continual.

*Aptitude to bear fruits.*—Normal.

*Resistance to frost.*—Good.

*Resistance to diseases.*—Good.

I claim:

1. A new and distinct variety of rose plant of the shrub class, characterised as to novelty by its fully double, dark crimson flowers with abundant and continual blooming the unusual blend of coloring and shaping of the flower being substantially as shown and described.

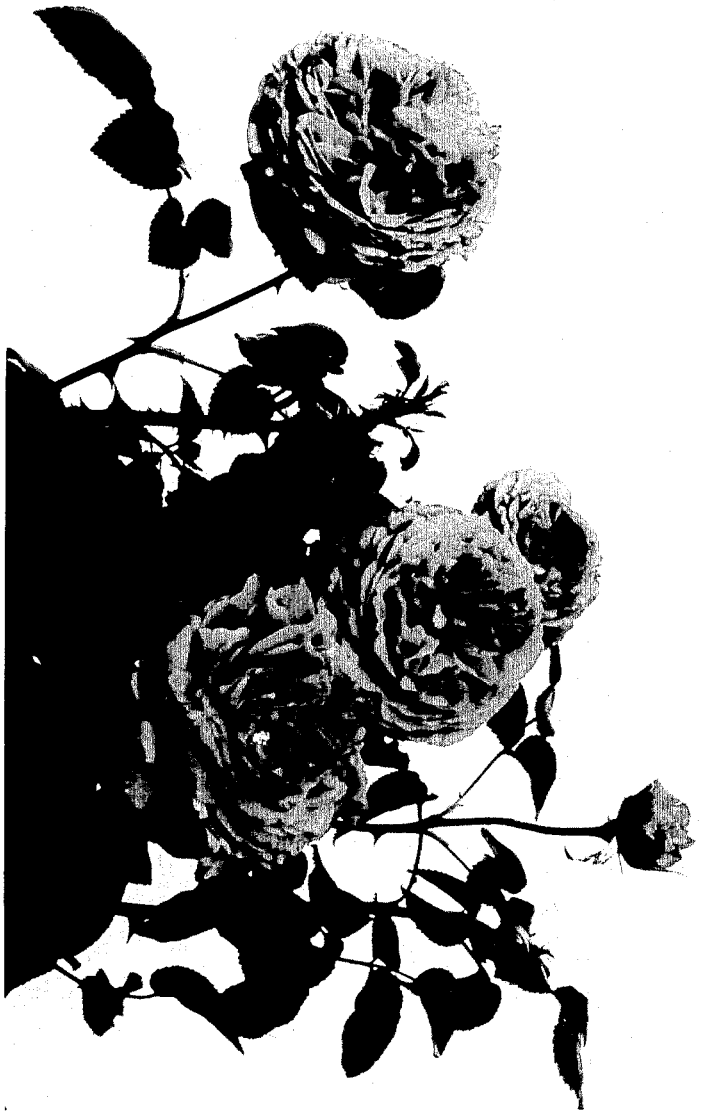

* * * * *